United States Patent
Wang et al.

(10) Patent No.: US 10,430,551 B2
(45) Date of Patent: Oct. 1, 2019

(54) SCAN DATA RETRIEVAL WITH DEPTH SENSOR DATA

(71) Applicant: Siemens Healthcare GmbH, Erlangen (DE)

(72) Inventors: Jiangping Wang, Champaign, IL (US); Kai Ma, West Windsor, NJ (US); Vivek Singh, Monmouth Junction, NJ (US); Mingqing Chen, Plainsboro, NJ (US); Yao-Jen Chang, Princeton, NJ (US); Shaohua Kevin Zhou, Plainsboro, NJ (US); Terrence Chen, Princeton, NJ (US); Andreas Krauss, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 271 days.

(21) Appl. No.: 15/513,669

(22) PCT Filed: Nov. 6, 2015

(86) PCT No.: PCT/US2015/059447
§ 371 (c)(1),
(2) Date: Mar. 23, 2017

(87) PCT Pub. No.: WO2016/073841
PCT Pub. Date: May 12, 2016

(65) Prior Publication Data
US 2017/0249423 A1    Aug. 31, 2017

Related U.S. Application Data

(60) Provisional application No. 62/076,389, filed on Nov. 6, 2014.

(51) Int. Cl.
G06T 17/20 (2006.01)
G06T 7/33 (2017.01)
(Continued)

(52) U.S. Cl.
CPC .......... *G06F 19/321* (2013.01); *A61B 5/1079* (2013.01); *A61B 6/032* (2013.01);
(Continued)

(58) Field of Classification Search
None
See application file for complete search history.

(56) References Cited

U.S. PATENT DOCUMENTS

2004/0002641 A1    1/2004  Sjogren et al.
2010/0111370 A1*   5/2010  Black .................. G06K 9/00369
                                                  382/111
(Continued)

FOREIGN PATENT DOCUMENTS

EP    2452649 A1    5/2012
EP    2727535 A1    5/2014
(Continued)

*Primary Examiner* — Yanna Wu

(57) ABSTRACT

In scan data retrieval, a mesh is fit (32) to surface data of a current patient, such as data from an optical or depth sensor (18). Meshes are also fit (48) to medical scan data, such as fitting (48) to skin surface segments of computed tomography data. The meshes or parameters derived from the meshes may be more efficiently compared (34) to identify (36) a previous patient with similar body shape and/or size. The scan configuration (38) for that patient, or that patient as altered to account for differences from the current patient, is used. In some embodiments, the parameter vector used for searching (34) includes principle component analysis coefficients. In further embodiments, the principle component analysis coefficients may be projected to a more discriminative space using metric learning.

12 Claims, 8 Drawing Sheets

(51) Int. Cl.

| | | |
|---|---|---|
| *A61B 6/03* | (2006.01) | |
| *G06F 16/583* | (2019.01) | |
| *A61B 6/00* | (2006.01) | |
| *A61B 5/107* | (2006.01) | |
| *G06K 9/00* | (2006.01) | |
| *G06K 9/62* | (2006.01) | |
| *G16H 50/50* | (2018.01) | |
| *G06F 16/56* | (2019.01) | |
| *G06F 19/00* | (2018.01) | |
| *G16H 50/70* | (2018.01) | |

(52) U.S. Cl.
CPC .............. *A61B 6/488* (2013.01); *A61B 6/544* (2013.01); *A61B 6/545* (2013.01); *G06F 16/56* (2019.01); *G06F 16/5838* (2019.01); *G06K 9/00214* (2013.01); *G06K 9/00369* (2013.01); *G06K 9/621* (2013.01); *G06T 7/344* (2017.01); *G06T 17/20* (2013.01); *G16H 50/50* (2018.01); *G06K 2209/05* (2013.01); *G06T 2207/10028* (2013.01); *G06T 2207/10081* (2013.01); *G06T 2207/30196* (2013.01); *G06T 2210/41* (2013.01); *G16H 50/70* (2018.01)

(56) References Cited

U.S. PATENT DOCUMENTS

| | | |
|---|---|---|
| 2013/0345543 A1 | 12/2013 | Steibel, Jr. et al. |
| 2014/0226794 A1 | 8/2014 | Quam et al. |
| 2014/0355735 A1* | 12/2014 | Choi ...................... A61B 6/544 378/8 |
| 2015/0213646 A1 | 7/2015 | Ma et al. |

FOREIGN PATENT DOCUMENTS

| | | |
|---|---|---|
| GB | 2504711 A | 2/2014 |
| JP | 2014121364 A | 7/2014 |
| WO | 2014033614 A1 | 3/2014 |

\* cited by examiner

SCAN DATA RETRIEVAL WITH DEPTH SENSOR DATA

RELATED APPLICATIONS

This application claims the benefit of U.S. Provisional Application No. 62/076,389, filed Nov. 6, 2014. The entire contents of the provisional application are incorporated herein by reference, except that in the event of any inconsistent disclosure or definition from the present specification, the disclosure or definition herein shall be deemed to prevail.

TECHNICAL FIELD

The present teachings relate generally to scan data retrieval, such as retrieving similar cases.

BACKGROUND

To reduce unnecessary radiation, the medical image scan happens only to the pre-selected regions of the patient. Because of the variation in patient body shapes, body sizes, clothing, and the like, a technician operating a medical imaging scanner may be faced with the difficult task of trying to determine, roughly, the hidden location of an internal organ or region of interest in a patient. The current workflow of patient scan range planning is determined by the technicians from low-dose topogram images, which results in extra radiation of the patients. The technician then manually positions the patient such that the region of interest is optimally positioned with respect to the scanner. The manual patient positioning process is time-consuming and costly.

To improve the manual patient positioning process, motion-sensing input devices (e.g., Microsoft Kinect) are used for coarse initial patient setup verification and alignment. However, this approach involves aligning the patient on a table based on a previously obtained CT scan in the diagnostic phase. Thus, a prior medical imaging scan (e.g., which may have already necessitated some degree of manual patient positioning and/or radiation exposure) is a prerequisite to this approach.

Generation of a synthetic topogram from an optical RGB-D sensor may assist the technicians to determine the patient's scan range without extra radiation. This method relies on searching for the best match between the queried RGB-D data and a large CT dataset, so it may take hours of computation time. In other approaches, patient re-alignment is used with the optical sensor, but requires that the surface data to belong to the same patient.

SUMMARY

By way of introduction, the preferred embodiments described below methods, systems, and computer readable media with instructions for scan data retrieval. A mesh is fit to surface data of a current patient, such as data from an optical or depth sensor. Meshes are also fit to medical scan data, such as fitting to skin surface segments of computed tomography data. The meshes or parameters derived from the meshes may be more efficiently compared to identify a previous patient with similar body shape and/or size. The scan configuration for that patient, or that patient as altered to account for differences from the current patient, is used. In some embodiments, the parameter vector used for searching includes principle component analysis coefficients. In further embodiments, the principle component analysis coefficients may be projected to a more discriminative space using metric learning.

In a first aspect, a method is provided for scan data retrieval. Depths are measured relative to a surface of a patient with a depth sensor. A first mesh is fit to the depths. Based on similarity, a search for a second mesh in a database of meshes fit to medical scan data from different patients is performed. A medical scanner is configured to scan the patient. The configuration is based, at least in part, on scan parameters derived from one of the different patients corresponding to the second mesh.

In a second aspect, a method is provided for scan data retrieval. A first object is parameterized with principle component analysis coefficients. A machine-trained projector projects the principle component analysis coefficients into a metric space. Similarity of the first object with another object is found based on values for the metric parameters projected from the principle component analysis coefficients. The similarity is indicated.

In a third aspect, a system is provided for scan data retrieval. A camera is configured to detect a surface of a body. A processor is configured to derive a first representation of a shape of the surface with a machine-trained projector and to match the representation with a second representation from a plurality of representations of surfaces of other bodies derived with the machine-trained projector. A display is configured to indicate the match of the first representation with the second representation.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

An efficient and parameterized approach is provided for retrieving medical scan images from red green blue-depth (RGB-D) or other depth sensor data. In one embodiment, given an input RGB-D snapshot of the patient, the closest computed tomography (CT) volume data within a pre-collected CT database is found. With proper deformations, the retrieved closest CT volume may be used to reflect the current patient body configuration and assist the technicians to determine the actual scan range and/or iso-center. In normal cases, two similar body shapes should have similar inner-organ positions.

A synthetic medical scan or topogram image of any patient is generated based on a snapshot from the optical depth sensor. The synthetic topogram image may be generated in less than one minute. A scan range for any patient is determined using a snapshot from the optical depth sensor. The iso-center of the scan body of the patient may be determined.

Figure 1:
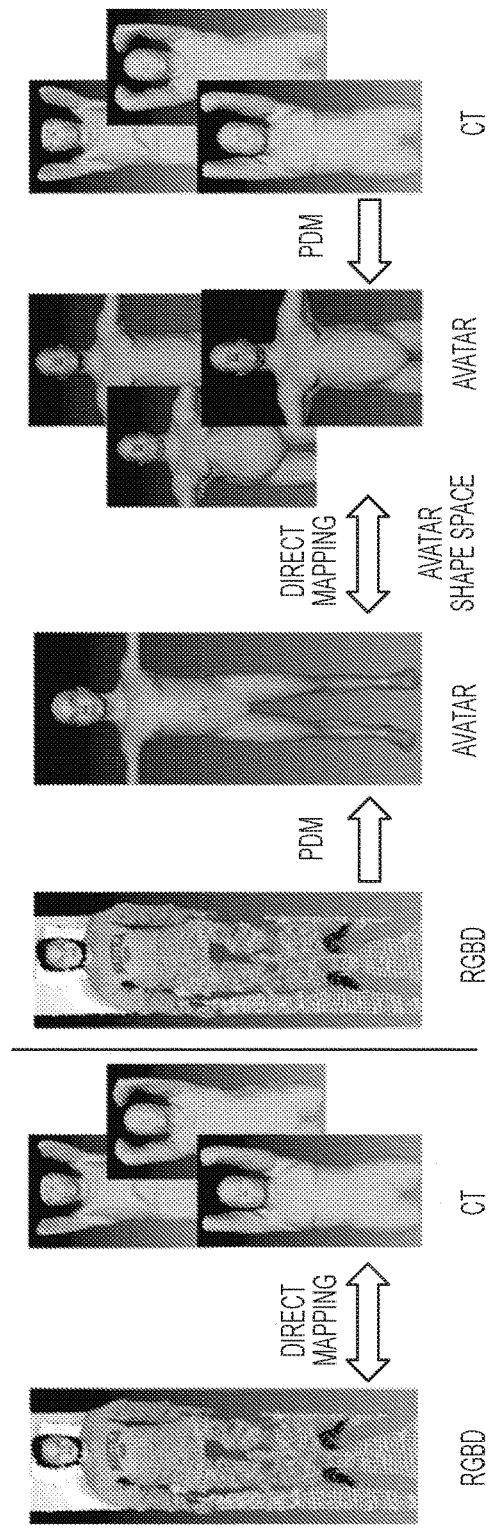
FIG. 1 illustrates use of mesh fitting to compare depth data to scan data, according to one embodiment.

Direct mapping between the RGB-D and the CT volume data may take hours for computation, depending on the size of the CT database. Moreover, the direct mapping accuracy might be tampered due to the differences between two data modalities. To resolve these problems, a Parameterized Deformable Model (PDM) algorithm is applied to both data sources to capture the shape information and then search for the optimal mapping within the shape parameter space. The similarity of two human bodies is determined by the body shape, not the body pose. A simple example of this indirect mapping is shown in FIG. 1. The left side of FIG. 1 shows a conventional method that maps the RGB-D directly to the CT data. Due to the difference in data and comparing many values, this approach is prone to errors and computational burden. The right side of FIG. 1 shows indirectly mapping the two data sources by fitting synthetic avatar models to both sources. This use of mesh fitting handles mapping errors due to the pose variations and sensor noise. Since the meshes may be parameterized into a low dimensional 1D vector, the search query is more efficient.

Figure 2:
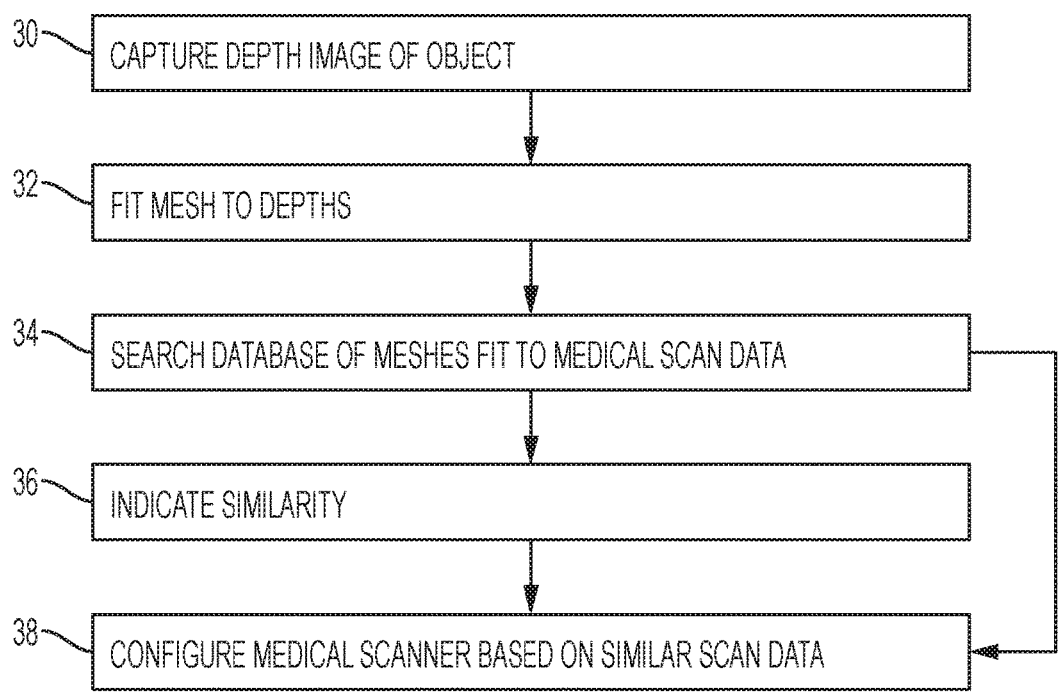
FIG. 2 is a flow chart diagram of one embodiment of a method for scan data retrieval.

FIG. 2 shows one embodiment of a method for scan data retrieval. The method includes fitting mesh to depth data, such as from a non-radiating optical depth camera, of a current patient. Information from the fitted mesh is used to search a database of information from meshes fitted to representative medical scan data. For example, meshes were previously fit to the skin represented by computed tomography (CT) data of a variety of different patients. The more or most similar one of the different patients to the current patient is found. This match is indicated and/or used to configure the medical scanner for scanning the patient.

Figure 3:
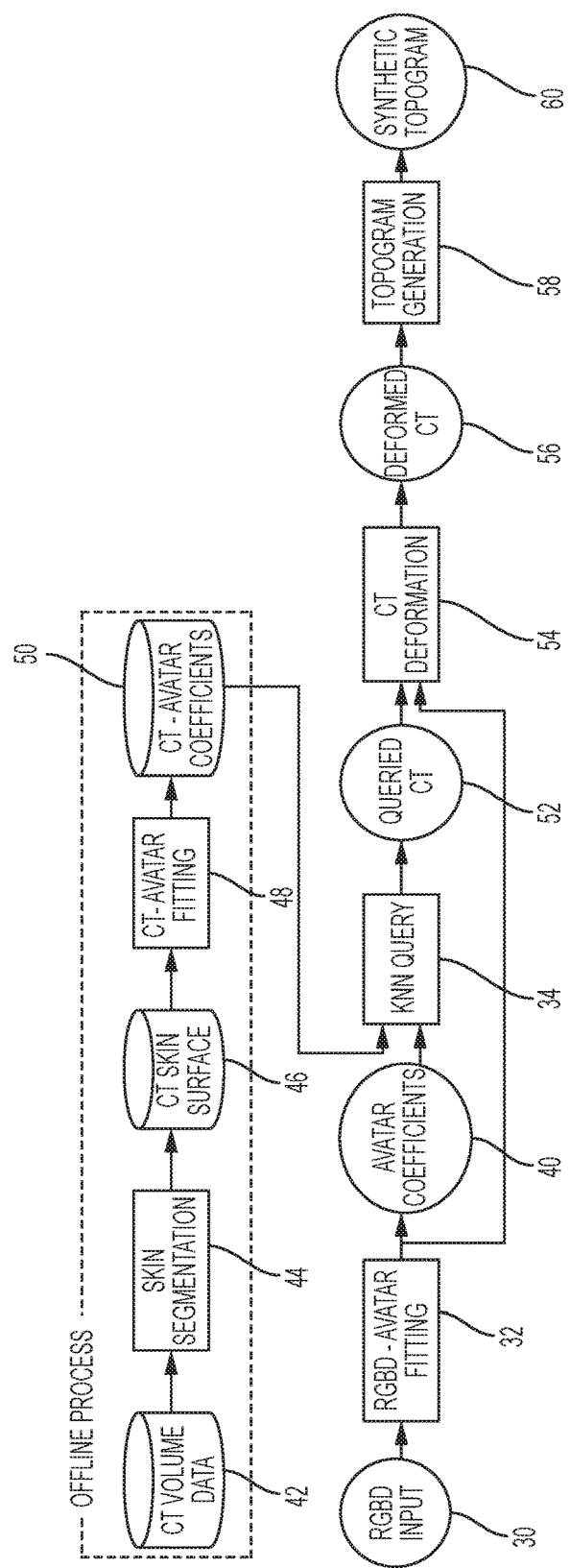
FIG. 3 is a flow chart diagram of a method for scan data retrieval for configuring a computed tomography scanner.

FIG. 3 is a flow chart diagram of a method for scan data retrieval for configuring a CT scanner. FIG. 3 is a more specific embodiment of the method of FIG. 2. FIG. 3 shows a workflow of a proposed framework. The framework includes an offline database creation process (e.g., acts 42-50) and an independent online process (e.g., remaining acts). The online process may be further divided into 4 components, which are RGB-D avatar fitting (e.g., acts 30-32), KNN data query (e.g., acts 40, 34, 52), CT deformation (e.g., acts 54 and 56) and synthetic topogram generation (e.g., acts 58 and 60). Topogram images for any current patient are generated from a red green blue-depth (RGB-D) snapshot of the patient.

The methods of FIGS. 2 and 3 may include additional, different, or fewer acts. For example, the indication and/or configuration of acts 36 and/or 38 are not performed. Different uses of the identification of one or more similar patients may be performed. As another example, any of the additional acts of FIG. 3 are performed in the method of FIG. 2. The acts for creating the database from a variety of patient shapes, sizes, and/or poses may be performed without the online acts for a current patient. The acts for the current patient may be performed without the fitting for the database where the database already exists.

In the examples discussed herein, computed tomography is used. Performing a scout scan in computed tomography to obtain a topogram may result in additional radiation being applied to the patient. The use of the depth data may avoid this. In other embodiments, the medical scan data is for positron emission tomography (PET) or single photon emission tomography SPECT). Rather than using computed tomography with PET or SPECT for positioning or to allow a lesser dose of radiopharmaceutical, finding similar patients using fit depth data is performed. In yet another embodiment, the methods are used for magnetic resonance to avoid the time required for any additional magnetic resonance scan.

The acts are performed in the order shown or a different order. For example, act 38 is performed prior to act 36. The offline or database creation acts may be performed before or after the online acts. The creation of the topogram acts may be performed prior to the online acts, such as during creation of the database, where additional morphing for the current patient from the similar patient (e.g., acts 54 and 56) is not performed.

In act 30, a depth image of an object is captured. A depth sensor measures depths relative to a surface of a patient. Any depth sensor may be used. The depth sensor provides three-dimensional sensor image data or depth data. In some embodiments, the depth data is captured via a camera. Any now known or later developed depth camera may be used, such as stereo cameras, structured-light devices (e.g., Microsoft Kinect, ASUS Xtion), time-of-flight devices (e.g., Creative TOF cameras), and combinations thereof. In some embodiments, the three-dimensional sensor image data further includes color image data (e.g., an RGB image). Any optical depth camera may be used to measure the surface of the patient, with or without clothes.

The placement of one or more cameras in the medical image scanning room (e.g., a CT scanning room, a PET scanning room, a MR scanning room, and/or the like) may be determined empirically in order to achieve optimal performance of the analytics. Various factors that may influence performance include, for example, the ease and/or expense of sensor installation, patient visibility constraints (e.g., the quality of the obtainable data), and sensor noise characteristics. For example, with structured-light devices and time-of-flight devices, noise tends to increase as distance from the sensor increases. Moreover, depending on wavelength, noise may also increase in close proximity to the sensor. Thus, sensor noise characteristics may be balanced against the field of view of the sensor when determining placement of a sensor.

Figure 4:
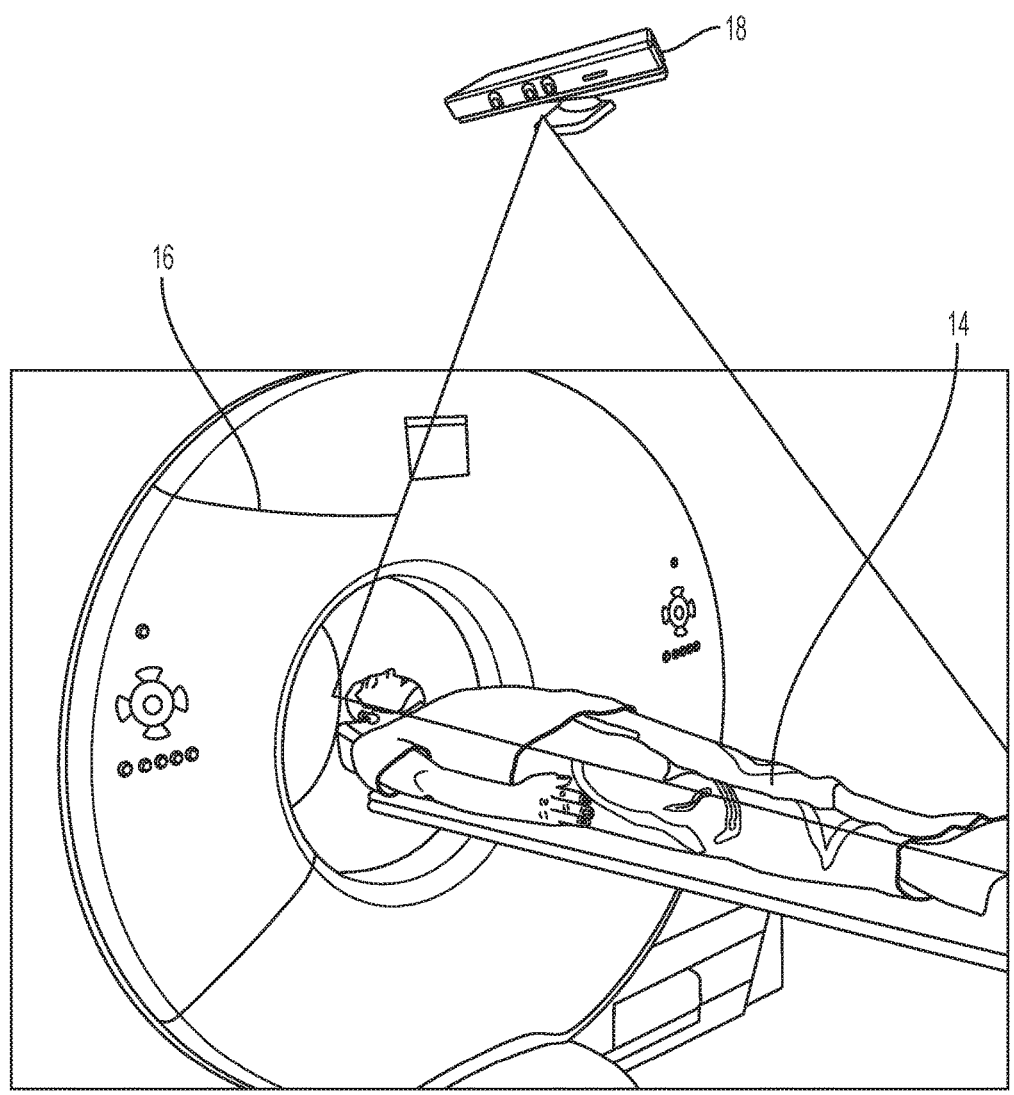
FIG. 4 shows an example of a camera for measuring a surface of a patient to be medically scanned.

To achieve reliable surface reconstruction from depth images, the cameras may be mounted such that the cameras have an unobstructed view of the patient lying on the patient table. Depending on the sensor noise characteristics (e.g., image quality and/or resolution of captured depth-image), the camera(s) may be mounted close to the scanner table while still being able to keep the entire or majority of the patient within the camera view. FIG. 4 shows an example placement of the depth sensor 18 relative to the patient 14 and the CT scanner 16. The camera depth sensor 18 is positioned on the ceiling above the patient table and in front of an entry into the bore of the CT scanner 16. In other embodiments, the camera depth sensor 18 is positioned on the gantry of the CT scanner 16.

More than one camera may be used, such as a first camera positioned on the ceiling directly above a patient table, and a second camera positioned at one end of the patient table. The two locations—overhead and angled—each have their advantages and disadvantages. For example, with an overhead camera, the analytics problem is more constrained and results that are more accurate may be obtained. However, the overhead camera presents challenges from an installation perspective since it is to be mounted on the ceiling. By contrast, the angled camera may have a lower installation overhead (e.g., the camera may even be attached to the gantry at the time of shipment). However, with the angled view, some patient data may be obscured.

In one embodiment, the depth measurements from the sensor provide a 3D point cloud of the patient. The 3D point cloud may be reconstructed and used for further processing. Data may also be captured from both cameras and fused in order to obtain a more accurate 3D point cloud. Since the two cameras are fixed, the cameras may be stereo calibrated (e.g., camera positions may be estimated relative to one another). Given the calibration information, the data from the two cameras may then be combined to obtain a denser point cloud representation of the scene.

Referring again to FIGS. 2 and 3, a processor fits a mesh to the depths measured by the depth sensor in act 32. The 3D point cloud represents a surface of the patient. The surface may be the skin or clothing of the patient, but generally conforms to the pose, shape, and size of the patient. The processor fits the mesh to the depths to morph a patient model to the current patient. Once a patient is positioned on the bed, the patient is imaged or scanned with the depth sensor so that the mesh may be fit to the patient. The fitted mesh is an avatar template model for that patient.

Any mesh may be used. In one embodiment, the mesh is fit to the patient for then determining characteristics of the patient from the fit mesh. In another embodiment, the mesh is a parameterized deformable model. Fitting the mesh results in values for the parameters of the deformable model. The deformable human body mesh is fit, providing projected mesh parameters in a low-dimensional sub-space to improve discriminability across different persons.

The surface of the patient detected with the optical depth or other depth sensor is parameterized. The parameterization may be providing locations for nodes of a mesh, such as a triangular, diamond, polygon, or other mesh. The parameterization may include further information, such as principle component analysis coefficients. By fitting the parameterized deformable mesh to the surface of the patient or other object, values for the parameters are provided. The values for the parameters act as a signature or fingerprint for that fit mesh.

Figure 5:
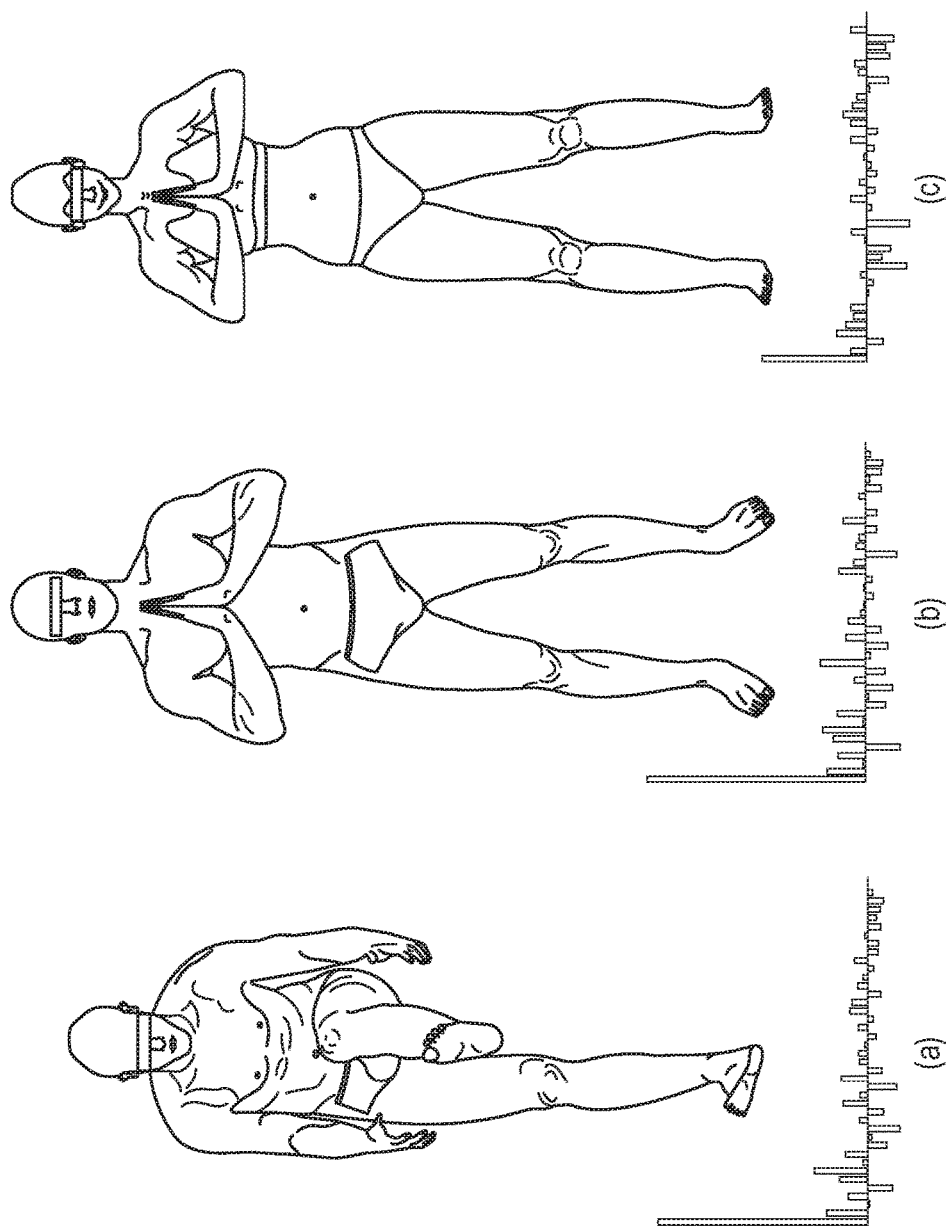
FIGS. 5A-C show example meshes and corresponding principle component analysis coefficients.

FIGS. 5a-c show three example fit meshes and corresponding parameters (e.g., shown as bar charts) for the fit meshes. FIGS. 5a and 5b are meshes from the same person in a different pose. FIGS. 5b and 5c are meshes from different persons in a similar pose. Notice that the values of the parameters for FIG. 5a are more similar to FIG. 5b in comparison to FIG. 5c.

The avatar or parameterized deformable model models the pose and body shape parameters independently. Since the values of the parameters are derived only from the shape parameters, the model is robust to pose perturbations. Following this, the parameters represent the holistic shape information based on the model fitting, which is robust to missing mesh data as well as local noise. This is practically relevant since a complete 360-degree view body scan of individuals may not be performed. Different parts of the patient may be obscured, depending on the pose dictated by injury and the position of the camera.

Given a 3D scan of an object as viewed from one or more directions, the shape matching of the mesh provides a unique shape characterization of the object. These parameters serve as the key for matching. The ideal shape descriptor or collection of parameters should be compact (for fast search) and exhibit invariance to all other deformations beyond shape and/or size. For the human body shape, it is particularly important to deal with the variations due to pose changes. The parametrized deformable mesh (PDM) model of the human body decouples the human pose and shape perturbations and models them separately. Therefore, the shape model factorizes the deformations caused by changes in intrinsic shape (height, size, belly thickness, etc.) from deformations caused by changes in pose (rigid transformations of body parts).

In one embodiment, the fitting is performed in three or more stages. A plurality of landmarks represented in the depths relative to the surface of the patient is detected. A template mesh is deformed to the landmarks as a coarse fitting. The template mesh as deformed to the landmarks is then fit to the depths as a fine or refined fitting.

Given a 3D depth image, the landmark detection determines the locations of pre-defined body joints. Machine trained classifiers, template matching, or other detection of one or more landmarks may be used. The landmarks are any distinguishable characteristic of the object, such as neck, shoulders, nose, hip, elbows, or other body part.

Given the landmark detection results and the corresponding joints or landmark labels of the avatar template, the coarse fitting deforms the avatar template and generates a new mesh that has similar pose as the actual patient from the RGB-D image. The coarse deformation is of the landmarks to establish pose. Different parts of the mesh may be linked to different landmarks, so that positioning two landmarks relative to each other defines the corresponding locations of the mesh. For example, the foot, knee, and hip landmarks represented in FIG. 5a are positioned. The parts of the mesh between each of the landmarks are positioned based on the landmark position. This provides a coarse pose-based fitting.

Based on these coarse fitting results, the fine fitting continues to deform the template avatar towards an optimal body pose and shape. The template mesh as posed is then fit to the 3D depth data. Any fitting may be used, such as a non-rigid iterative closest point fitting with any bending and/or spring constraints. A least square or other fit criterion or criteria may be used. The registration-optimization loop refines the resulting avatar mesh iteratively. Given the correspondences, the template mesh is deformed to minimize the 2-norm. The deformed template mesh is then used to determine new correspondences and this process of registration and optimization is repeated until convergence (i.e., average distance is below a certain score or maximum number of iterations are reached).

The avatar or fit mesh provides values for the parameters as an output. Rather than using the mesh itself, a fewer number of parameters are defined to represent the shape and/or size of the fit mesh independent of the pose. Any simplification may be used. In one embodiment, a distance, curvature, area, volume, or other measure between defined points on the mesh are used. For example, the parameters are the waist width, waist curvature, chest width, chest curvature, shoulder width, neck to pelvis length, and/or other measurements of the fit mesh.

In another embodiment, the parameters are principle component analysis coefficients. Rather than being measures relative to specific body parts, the parameters are of the shape and/or size of the mesh regardless of specific body parts. To create the deformable mesh with embedded parameters, the shape deformations use principle component analysis over a large dataset with shape and/or size variations. POSER or another shape fitter may be used. Besides being able to efficiently generate a large training dataset with accurate point wise correspondences, one additional benefit is the reduction in training complexity since POSER allows shape perturbations without changing the pose. Any size training set may be used, such as 1,000 poses and 600 shapes. Other shape fitters than POSER may be used.

Given the shape training dataset, the shape affine matrix $S_i$ for each triangular mesh data i may be obtained by solving the quadratic function $$\underset{S^i}{\operatorname{argmin}} \sum_k \sum_{j=2,3} \|S_k^i \hat{v}_{k,j} - v_{k,j}^i\|^2 + w \sum_{k_1,k_2 adj} \|S_{k_1}^i - S_{k_2}^i\|^2 \quad (1)$$

where k represents the triangle index, vk,j represents the jth edge in kth triangle of ith training mesh, $\hat{v}$ hat represents the edges in the avatar template mesh, and w is the parameter balancing the two parts of the optimization objective function, where the left term tries to minimize the data errors while the right term aims to add smoothness to avoid abrupt geometry changes within nearby triangles. The affine matrices may be further decomposed into a linear combination of Eigen-vectors U and mean-vector μ by using principle component analysis, as represented by:

$$S^i = F_{U,\mu}(\beta^i) = U\beta^i + \mu \quad (2)$$

By changing the values of the principle component analysis coefficient vector ß, any body shape in the learned manifold may be recovered. Although there is no explicit interpretation of each dimension to a semantic definition, the first few dimensions of ß correspond to the global shape perturbations in the shape training set (e.g., gender, height, body size, and etc.). The following dimensions of ß capture more and more subtle perturbations.

The fitting accuracy of the parameterized deformable mesh depends on the number of principle component analysis coefficients used to model the shape parameters. While more dimensions may model body deformations in greater detail, the additional dimensions also increase time complexity and the possibility to fit small, noisy perturbations in the data. Hence, the choice of the number of coefficients is important. For example, 60 coefficients retain 98% of the energy, helping suppress noise without losing most of the shape deformation information. A greater or fewer (e.g., 20 or 40) number of coefficients may be used Referring to FIG. 3, after fitting, the avatar fitting module of the processor returns a shape description vector in act 40 (see FIG. 3). The fitting defines the values of the principle component analysis coefficients. The relationship was learned, so the fitting to any given patient outputs coefficients. The values of these coefficients and/or other parameterization values provide measures specific to the patient based on the depth data representing the surface of the patient.

The shape description vector is used for searching a database. The vector or group of parameters has a same size as used for the database. The same parameters are determined for the examples in the database, so the same number and type or same collection of parameters are used to parameterize a given patient and the different patients of the database.

The database is created in an offline or other process. The database provides a link to medical scan data. In the example of FIG. 3, the medical scanning is CT. In act 42, medical scan data representing a variety of patients is acquired. The CT data represents volumes of patients in various different shapes (e.g., size and/or curvature). The collection of representative data is for a wide variety of patients. For more common shapes and/or sizes, a greater refinement in variation may be used.

Given a RGB-D or other depth snapshot of a current patient, a pre-built database is queried using the parameter values for the current patient in order to return a CT mesh that is close to the current patient's body shape. The pre-built database covers the variations of body shape as much as possible. It may not be feasible to store and query tens of thousands or more real world different patients. Instead, a smaller set representing a range of various shapes and sizes is used, such as about 1,000 CT volumes of human upper bodies over a variety of age, ethnicity, and body shapes.

For fitting, the skin of the CT volumes is segmented in act 44. Any now known or later developed segmentation may be used. For example, thresholding is applied to identify the return from or locations of skin. As another example, a gradient is calculated as the skin-to-air or clothing transition is greater than tissue-to-tissue transitions. A threshold is applied to the gradients to identify the skin location. Filtering may be applied to the segmented results. The result with or without filtering are CT-based skin surfaces for a variety of patients of the database. The surfaces are output in act 46.

In act 48, meshes are fit to the medical scan data. A processor fits a polygon mesh, such as a parameterized deformable mesh, to the CT data representing a skin of a patient. To create the database, the meshes are fit to the different patients. The mesh fitting is the same or different than applied for the current patient in act 32. For example, the parameterized deformable model is fit to the skin segments for the different patients, creating a CT-based avatar with corresponding values for coefficients in act 50. The avatar model fit to each of the different CT volumes outputs the shape parameters of the avatar to represent the body shape of the patient. The output is a low-dimension shape description vector that represents the body shape of the deformed avatar. If the avatar fits the CT skin surface mesh well, then the output shape vector accurately describes the CT skin surface, which reduces the shape parameters of the skin surface mesh from hundreds of thousands to a much less number.

Overall, the database creation process includes skin segmentation, avatar fitting and shape coefficients extraction. The output of this process is a two-dimensional matrix, where the number of rows equals to the number of different patients (e.g., about 1,000) and the number of columns is the number of shape description vector measures (e.g., 60 principle component analysis coefficients). Other output formats may be used. After the offline process, the set of original CT volumes is represented by the matrix and stored in a Kd-tree structure. Other structures may be used.

In act 34, the matrix or database is searched. A processor searches for a mesh in the database of meshes fit to medical scan data from different patients to find a mesh most or sufficiently similar to the current patient. Any mesh-based search, such as using a sum of absolute differences between meshes, may be used. To reduce computation or processing, the values of the shape parameters are instead used. In order to get the closest CT mesh from the database, the shape description vector generated from the RGB-D avatar-fitting is compared to all shape vectors in the database. The database shape descriptor vector that has the minimum distance to the RGB-D shape descriptor is found. The database mesh with the closest values of the parameters to the values of the parameters of the current patient is found.

The search compares the values of parameters representing the current patient (i.e., values from fitting to the depth data) with the values for the parameters representing the patients of the database (i.e., values from fitting to the medical scan data from the different patients). The comparison is of measures of the patients' shape and/or size reflected in the parameters. In one embodiment, the principle component analysis coefficients are compared as the parameters.

Any measure of similarity for finding the match may be used. The distance function (i.e., similarity) may be Euclidean distance, Mahalanobis distance, or other measure. In one embodiment, a K Nearest-Neighbor (KNN) data query is used. For efficient nearest-neighbor searching, the Kd-tree data structure is used to store the database and query the input.

Rather than finding a closest, a sufficiently close match may be found. For example, a measure of difference or similarity is calculated. The measure is compared to a threshold for sufficiency. If the difference is small or the similarity great as determined by the threshold, then the match is found and searching may cease.

To increase the discriminative ability of the shape descriptor, a metric space may be used. The values of the parameters for the different avatars are projected to the metric space for comparison in the metric space. The projector is trained to better separate or discriminate between shapes with a same, fewer, or greater number of values (e.g., input 60 values to projection, which outputs 60, more, or fewer values).

The projection matrix is obtained using ranking-based metric learning in a batch. The learning is performed once to provide a machine-learnt matrix that efficiently increases the discrimination of values to be compared. In other embodiments, online learning is used where additional examples are regularly or occasionally added to the training data, increasing the size of the database from time to time for refining the projector (e.g., on-going learning). Alternatively, the projector is relearnt as desired.

The mesh parameters are projected to a low-dimensional manifold, such that the distance between meshes from different persons and/or categories is maximized while minimizing the distance between meshes from a same person and/or category. This projection matrix is obtained using a ranking based distance metric learning algorithm.

The projector is machine-trained. The learnt projector provides values for metric parameters projected from the principle component analysis coefficients or other values of parameters determined from the fit meshes. Given a human body scan, the pose and shape are decoupled by the parameterized deformable model. The parameterization of the mesh provides the holistic body shape information onto a low dimension principle component subspace, yielding a set of coefficients $\beta$ in equation (2). These coefficients may themselves be used as a shape descriptor for matching body shape with Euclidean metric. The discriminability of the descriptor may or may not be sufficient in practical applications. The shape coefficients may be projected to another manifold, such that the distance between meshes from different persons is maximized while the distance between meshes from a same person is minimized.

In ranking-based metric learning, for a pair of descriptors $(x_j, x_k)$, the Mahalanobis distance is measured by:

$$D_M^2(x_j, x_k) = (x_j - x_k)^T M (x_j - x_k) \quad (3)$$

where M is a symmetric positive semi-definite (PSD) matrix. Since the matrix M may be decomposed as $M = L^T L$, the Mahalanobis distance may be interpreted as the Euclidean distance in a linearly transformed feature space (i.e., $D_M^2(x_j, x_k) = \|(x_j - x_k)\|_2^2$.

In order to learn a metric or pseudo metric for 3D shape matching, triplet constraints are used for supervision. Paired constraints may be used. Triplet constraints carry pairwise similarities between three data items of a set. In a triplet $(x_i, x_i^+, x_i^-)$ annotation, $x_i$ is considered more similar to $x_i^+$ than $x_i^-$. One reason to use triplets is that in most cases, very few (if not one) 3D shape data are provided for the same subject and thus lack pairwise constraints. The other reason is triplet constraints contain more similarity side information than pairwise constraints on the same dataset.

Given the triplet constraints, either batch or online metric learning is performed. A maximum margin criterion is used, but other criteria may be used. For maximum margin, the distance between more similar pairs $(x_i, x_i^+)$ is less than that between dissimilar pairs $(x_i, x_i^-)$ by a large margin. This idea is similar to Large Margin Nearest Neighbor (LMNN), but class labels of the data are not needed. The aim is to learn a metric purely based on triplet constraints, while LMNN optimizes kNN for classification.

A positive semi-definite (PSD) matrix is solved. In an ideal setting, there might exist a matrix M, such that for any triplet $(x_i, x_i^+, x_i^-)$:

$$D_M^2(x_i, x_i^-) > D_M^2(x_i, x_i^+) + 1 \quad (4)$$

Similar to Support Vector Machine (SVM), a soft margin is used for an inseparable case, which amounts to minimizing hinge loss, as represented by:

$$l_i(M) := [1 + D_M^2(x_i, x_i^+) - D_M^2(x_i, x_i^-)]_+ \quad (5)$$

where $[z]_+ = \max(0, z)$. On the other hand, low-dimensional parameterized deformable mesh shape descriptors are employed after principle component analysis, so the learned metric should not be distorted from the identity matrix too much. Taking into account the above constraints, the batch algorithm is given by:

$$\min_{M \succeq 0} \frac{\lambda}{2} \|M - I\|_F^2 + \frac{1}{N} \sum_S \ell_i(M) =: F(M) \quad (6)$$

where $S = \{(x_i, x_i^+, x_i^-)\}$ is the set of triplets, $|S| = N$.

A generic solver for semi-definite programming employs an interior point and does not scale well with a large number of constraints, as is the case in equation (6). An efficient stochastic sub-gradient descent algorithm is used to solve the optimization, as shown in Algorithm 1, below, where $\eta_t$ is the learning rate and output M is the minimizer of F(M). F(M) is computed every j epochs in the late stage of learning where j ranges from dozens to hundreds, depending on the total size of mini-batches.

---

Algorithm 1 Mini-batch stochastic subgradient descent
algorithm for solving optimization in Eq. (6)

---

1: Input: $\mathcal{S}$, $\lambda$ and T.
2: Initialization: $M_1 = I$
3: for t = 1, 2, ..., T do
4:    Randomly choose $\mathcal{S}_i \subseteq \mathcal{S}$, $|\mathcal{S}_i| = K$
5:    Set $\mathcal{S}_i^+ = \{(x_i, x_i^+, x_i^-) \in \mathcal{S}_i : 1 + D_{M_i}^2(x_i, x_i^+) - D_{M_i}^2(x_i, x_i^-) > 0\}$ Algorithm 1 Mini-batch stochastic subgradient descent
algorithm for solving optimization in Eq. (6)

6:
$$\nabla_i = \lambda(M_i - I) + \frac{1}{K}\sum_{S_i^+}(C_i(x_i, x_i^+) -$$

$C_i(x_i, x_i^-))$, where $C_i(x_i, x_i^+) := (x_i - x_i^+)(x_i - x_i^+)^T$
7: $M_{i+1} = M_i - n_i \nabla_i$
8: Decompose $M_{i+1} = U\Lambda U^T$
9: Project $M_{i+1}$ onto PSD cone, $M_{i+1} \leftarrow U\Lambda_+ U^T$,
where $\Lambda_+ = \max(0, \Lambda)$.
10: end for
11: Output: $\text{argmin}_{M \in \{M_1, M_2, \ldots, M_{T+1}\}} F(M)$ The learning may instead using online learning. In one embodiment, an online algorithm based on the Passive-Aggressive (PA) family of learning algorithms is used, but other approaches may be used. In the online setting, a triplet $(x_i, x_i^+, x_i^-)$ is observed at each time step i, which suffers a loss defined in equation (5). If $l_i(M)=0$, no loss occurs. Otherwise, the metric is updated. Denote by $M_i$ the matrix used for prediction at time step i.

In a separable case, there exists a matrix $M^*$ such that $l_i(M^*)=0$ for all i. Following the method in the Pseudo-metric Online Learning Algorithm, the orthogonal projection operation is used. Given $\forall W \in R^{d \times d}$ and a closed convex set $C \subset R^{d \times d}$, the orthogonal projection of W onto C is defined by $$\mathcal{P}_C(W) = \underset{W' \in C}{\text{argmin}} \|W - W'\|_F^2 \qquad (7)$$

For each time step i, the set $C \subset R^{d \times d}$ is defined as:

$$C_i = \{M \in \mathbb{R}^{d \times d} : l_i(M) = 0\} \qquad (8)$$

where $l_i(M)$ is defined in equation (5). Another constraint on M is that $M \succeq 0$. Denote by $C_a$ the set of PSD matrices, $$C_a = \{M \in \mathbb{R}^{d \times d} : M \succeq 0\} \qquad (9)$$

With the above definitions, the algorithm is comprised of two successive projections:

$$\tilde{M}_i = \mathcal{P}_{C_i}(M_i), \qquad (10)$$

$$M_{i+1} = \mathcal{P}_{C_a}(\tilde{M}_i). \qquad (11)$$

First, the current matrix $M_i$ is projected onto $C_i$ so the resulting $\tilde{M}_i$ will be the closest one to $M_i$ while achieving a zero loss on the received triplet at time step i. Second, $C_i$ is projected onto $C_a$ to ensure it is a metric. The projections may be performed analytically. The first projection is equivalent to solving the following constrained optimization problem, $$\tilde{M}_i = \underset{M}{\text{argmin}} \frac{1}{2}\|M - M_i\|_F^2, \text{ s.t. } l_i(M) = 0 \qquad (12)$$

which has a simple closed-form solution by using KKT condition:

$$\tilde{M}_i = M_i + \alpha_i V_i \qquad (13)$$

where $$V_i = (x - x^-)(x - x^-)^T - (x - x^+)(x - x^+)^T \qquad (14)$$

$$\alpha_i = \frac{l_i(M_i)}{\|V_i\|_F^2} \qquad (15)$$

Since $M_1$ is initialized to be identity matrix 1, $\tilde{M}_i$ is always symmetric and thus may be decomposed as $\tilde{M}_i = U_i \Lambda_i U_i^T$. By projecting $\tilde{M}_i$ onto PSD cone, $M_{i+1}$ may be derived as $M_{i+1} = U_i \Lambda_i^+ U_i^T$, where $\Lambda_i^+ = \max(0, \Lambda_i)$.

In theorem 1, let $(x_i, x_i^+, x_i^-)$ be a sequence of triplet instances. Assume that there exists $M^* \succeq 0$ such that $\forall_i \geq 1$, $l_i(M^*)=0$. Let R be an upper bound that satisfies $R \leq \|V_i\|_F^2$. Then, the following bound holds for any $T \geq 1$:

$$\sum_{i=1}^T l_i^2(M_i) \leq R\|M^* - I\|_F^2 \qquad (16)$$

For the inseparable case, there is no metric that separates the triplet instances by a large margin perfectly. This assumption is relaxed, so equation (10) is modified by solving the following optimization problem:

$$\tilde{M}_i = \underset{M}{\text{argmin}} \frac{1}{2}\|M - M_i\|_F^2 + C l_i^2(M) \qquad (17)$$

where C is an aggressiveness parameter that controls the trade-off between the loss on the triplet and the regularization. The above learning problem may be regarded as a matrix version of the PA-II algorithm, and has closed-form solution, given as:

$$\tilde{M}_i = M_i + \alpha_i V_i \qquad (18)$$

where $$\alpha_i = \frac{l_i(M_i)}{\|V_i\|_F^2 + \frac{1}{2C}} \qquad (19)$$

and $V_i$ is defined in equation (14).

Essentially, the solution has the same form as in equation (13) for the separable case, with some modification in $\alpha_i$. $M_{i+1}$ is obtained by projecting $\tilde{M}_i$ onto the PSD cone, following the same procedure s in equation (11).

For theorem 2, let $(x_i, x_i^+, x_i^-)$ be a sequence of triplets, and let R be an upper bound such that $\forall_i : R \geq \|V_i\|_F^2$. Then, for any matrix $Q \succeq 0$, the following bound holds for any $T \geq 1$:

$$\sum_{i=1}^T l_i^2(M_i) \leq \left(R + \frac{1}{2C}\right)\left(\|Q - I\|_F^2 + 2C\sum_{i=1}^T l_i^2(Q)\right) \qquad (20)$$

Either batch or online algorithms may be applied. Alternatively, both batch and online approaches are both applied, but independently or in conjunction with each other. In a practical setting where the human subjects in the dataset may change or grow over time, an initial metric may be obtained using the batch algorithm and then subsequently adapted using the online algorithm as new data becomes available.

The metric learning handles triplet annotations and learns the metric based on relative similarity constraints. Furthermore, algorithms and loss bounds may be derived for both separable and inseparable cases. The online algorithm is based on PA family of algorithms, so a metric in the form of a symmetric and PSD matrix is found.

Once learnt, the projector is applied to the values of the parameters. The projected outputs are compared to other projected outputs to find the similar case from the database.

In act 36, the similarity is indicated. Once the most or sufficiently similar medical scan data from the database is found, the match is output. Any indication of similarity may be provided, such as outputting the measure of similarity. The similarity may be indicated by outputting that a match has been found or other information about the match. For example, an image based on the matched medical data is output as an indication of the similarity. As another example, settings for configuring a medical scanner based on the match are output as an indication of the similarity.

Act 38 is an alternative or additional act to act 36. The results of the matching are used to configure a medical scanner. The similar scan data from the database is associated with or links to one or more settings for the medical scanner. Settings from the database, settings based on a topogram from the matched medical scan data, and/or settings derived from the medical scan data or database settings are used for the current patient.

FIG. 3 shows one example embodiment of act 38. In particular, acts 52-60 are performed. Act 38 is then performed based on the topogram of act 60. In alternative embodiments, acts 54 and 56 are not performed.

In act 52, the matched CT data is selected. Based on the match from the values of the parameters or the values in the metric space, a similar patient and corresponding CT data are identified.

In act 54, the matching CT volume is deformed. The medical scan data for the matching patient represents a similar but not identical patient. Where the patients have identical shape and/or size, then the deformation is not needed. Where there is a difference, then the processor deforms the medical scan data for the matched patient from the database to better emulate the current patient. Since the size of the database is limited, the retrieved CT mesh may not perfectly fit to the input mesh of the current patient. The retrieved CT mesh is deformed towards to the fitted RGB-D avatar mesh. Any deformation may be used, such as a 3D Thin Plate Spline (TPS).

The deformation deforms the surface or mesh, but also deforms interior portions of the volume. Through interpolation or other operations, the voxels are shifted or deformed to account for the current patient surface being different from the surface of the matched patient. As a result, a set of deformed medical scan data is output in act 56.

Figure 6A:
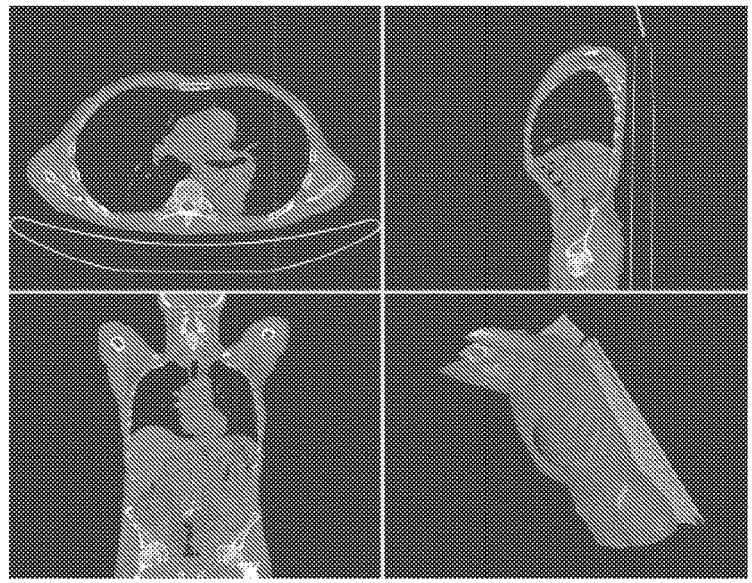
FIGS. 6A and B show example computed tomography images of a computed tomography volume before and after morphing to account for patient differences, respectively.
Figure 6B:
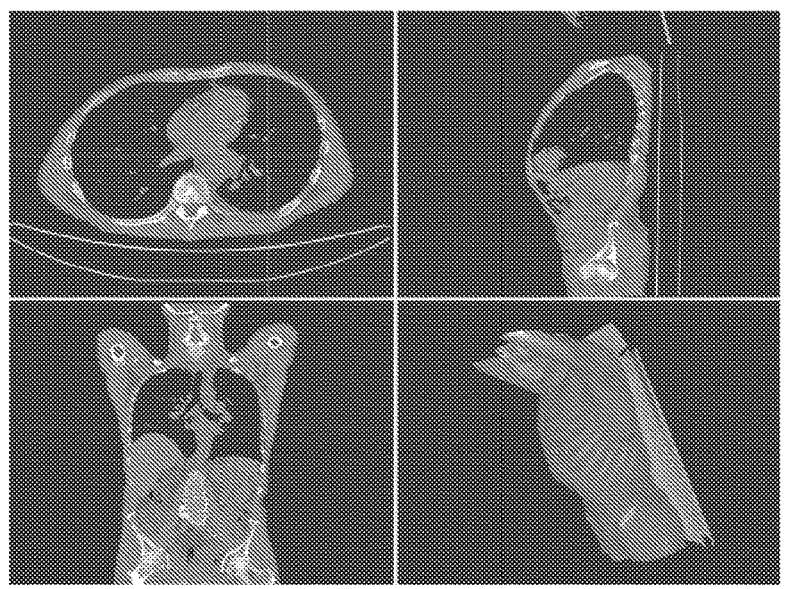

FIGS. 6A and 6B show an example. Both figures show three cross-section images and a perspective view three-dimensional rendering of a CT volume or data set representing the volume of the patient. FIG. 6A is a visualization of the CT volume before deformation. These images are generated from the matched medical scan data of the patient form the database. While the images may or may not be shown to the user, the images are shown to indicate the deformation. FIG. 6B visualizes the same CT volume (i.e., same scan data, cross-sections and perspective rendering) but after deformation using thin plate splines. Because of the deformation, the positioning or relative relationship of different parts of the body is shifted. The shift is based on differences between the matched CT skin surface and the depth-based surface of the current patient.

In act 58, the processor generates a topogram from the deformed volume. The medical scan data, as adjusted to account for differences from the current patient, is used to generate one or more images. For example, a synthetic CT topogram to emulate results from a scout scan is generated.

Any number of images may be generated, such as two images from orthogonal directions (e.g., lateral view and top view). The topogram is a cross-section, rendering, or projection. For example, data along lines projected in parallel or diverging as if from an x-ray source are blended or otherwise combined to represent an x-ray image through the patient. The resulting topogram is output for viewing by the user in act 60 and/or used for further medical scan system configuration.

Topogram images are used for scan range planning and generated from the low-dose CT scans. By generating synthetic topogram images from the deformed CT volume data, the actual topogram scan may be avoided, reducing the radiation applied to the current patient.

Figure 7A:
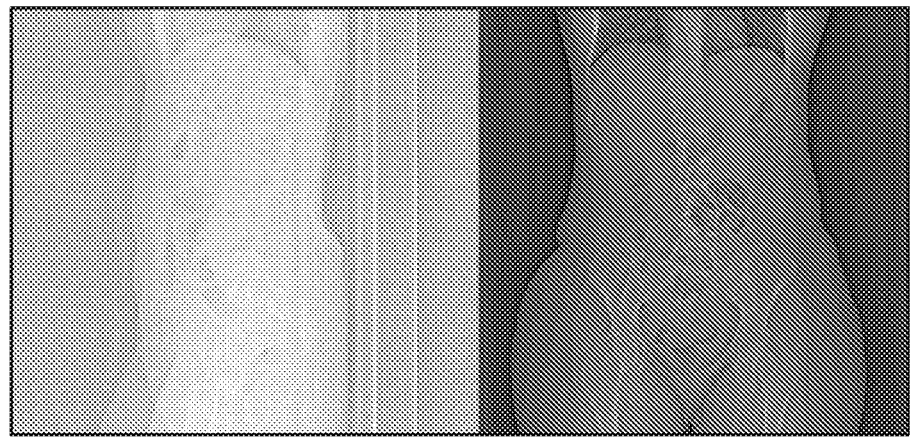
FIGS. 7A and B show example topograms from a scout scan and synthetic creation, respectively.
Figure 7B:
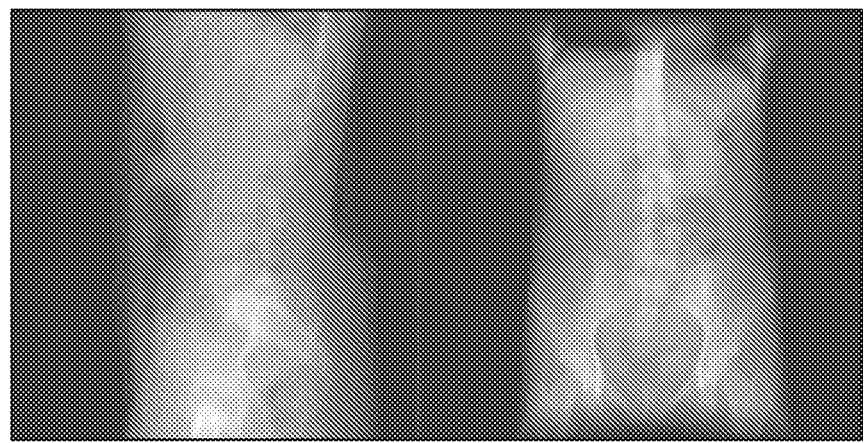

FIGS. 7A and 7B show some examples of topogram images. FIG. 7A shows lateral and top views of topogram images from a CT scan of a patient. FIG. 7B shows lateral and top views of a synthetic topogram generated from CT scan of a different patient.

In act 38, a medical scanner is configured to scan the patient. Using the synthetic topogram, the user configures one or more settings for scanning the current patient. For example, the scan range, iso-center, or both are configured based on the topogram. Alternatively, the settings for the matched patient from the database are used without or with separate generation of the synthetic topogram. The deformation may be used to adjust the values for the settings, such as to adjust for the iso-center and/or scan range. The scan parameters for scanning the current patient are configured based, at least in part, on the matched patient from the database.

Figure 8:
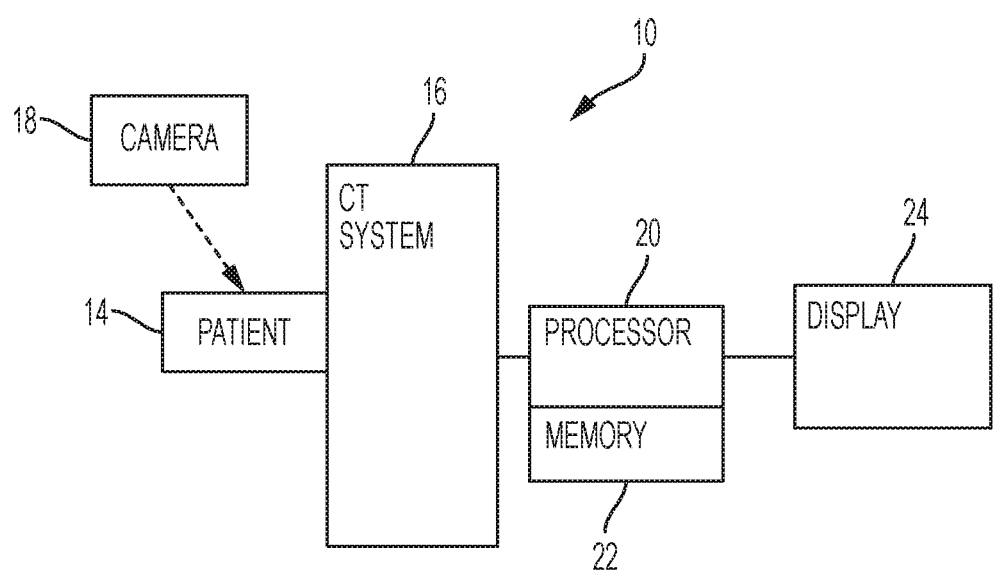
FIG. 8 is a block diagram of one embodiment of a system for scan data retrieval.

FIG. 8 shows one embodiment of a system 10 for scan data retrieval. The system implements the method of FIG. 1, FIG. 2, FIG. 3, or a different method. The system 10 is at a point of care for a patient 14, such as in a same room, hospital, or imaging center. In other embodiments, the processor 20, memory 22, and/or display 24 are at other locations, such as a different building. The system 10 is used to configure the CT system 16 or to provide information useful for the user to configure the CT system 16 without an x-ray-based radiation scout scan of the patient 14.

The system 10 includes one or more cameras 18, the CT system 16, the processor 20, the memory 22, and the display 24. Additional, different, or fewer components may be provided. For example, the display 24 is not provided. As another example, a user input device is provided for the user to configure the CT system 16 based on an image from the camera 18 and/or other image (e.g., synthetic topogram) on the display 24.

The processor 20, memory 22, and display 24 are part of the CT system 16 in one embodiment, such as being a CT workstation. In other embodiments, the processor 20, memory 22, and/or display 24 are part of a separate computer, such as a separate workstation, personal computer, laptop, or tablet. The processor 20 and/or memory 22 may be part of a server. In other embodiments, the memory 22 is a database separate from the processor 20.

The camera 18 is a depth sensor. Stereo cameras, structured light transmission with a camera as the sensor, time-of-flight sensor with a transmitter, or other now known or later developed sensor for determining depth is provided as the camera 18. In one embodiment, the camera 18 is an optical RGB-D camera.

The camera 18 is configured to detect a surface of a body or object. The surface is detected in three dimensions. The camera 18 captures an image from which depth may be derived. Alternatively, the camera 18 directly captures a 3D point cloud of different depth measurements. Image processing may be applied to remove background. Alternatively, the background remains and is dealt with as part of mesh fitting.

The patient 14 is positioned relative to the camera 18, such as on the bed of the CT system 16 while the bed is outside of the bore of the CT system 16. The camera 18 may be positioned to image the patient while the patient is within the bore. Where multiple cameras 18 are provided, the cameras 18 are directed to view the patient 14 from different directions. Depth data representing the surface of the patient is acquired from the different cameras 18 and used together to create a unified point cloud or surface representation.

The surface of the patient 14 is the skin of the patient. Alternatively, the surface of the patient 14 is clothing of the patient. The surface may be low pass filtered to remove high frequency variation. Depth information for combinations of skin and clothing may be detected.

The processor 20 is a general processor, central processing unit, controller, control processor, graphics processor, digital signal processor, three-dimensional rendering processor, image processor, application specific integrated circuit, field programmable gate array, digital circuit, analog circuit, combinations thereof, or other now known or later developed device for fitting, parameterizing, projecting, searching, matching, deforming, configuring, and/or generating a synthetic topogram. The processor 20 is a single device or multiple devices operating in serial, parallel, or separately. The processor 20 may be a main processor of a computer, such as a laptop or desktop computer, or may be a processor for handling some tasks in a larger system, such as in a medical imaging system. The processor 20 is configured by instructions, design, hardware, and/or software to be able to perform the acts discussed herein.

The processor 20 is configured to derive a representation of a shape of the surface. For a current patient, the processor 20 receives or accesses the depth data from the camera 18. A mesh, such as a parameterized deformable mesh, is fit to the depth data, creating a surface representing the patient to be imaged by the CT system 16. The processor 20 thus determines the values for various parameters representing the size and/or shape of the patient.

The processor 20 or a different processor creates a database of sets of the same parameters representing a variety of different patients. Rather than using depth data from a camera, the skin or other surface is segmented from medical imaging data, such as CT data. Meshes are fit to the segmented surfaces in order to determine the values of the parameters. Other information may also be linked to or included in the database, such as scan settings for the medical imaging system associated with each of the variety of patients.

The processor 20 is configured to match the surface representation from the current patient with a similar surface from the database. Rather than matching the fit meshes, the parameters representing the meshes are matched. One or more of the variety of patients or surfaces used for the database are selected after searching based on the similarity of the values for the parameters, such as principle component analysis coefficients. The search is for a patient with a similar size and/or shape, as parameterized by the fitted meshes.

The processor 20 may apply a machine-learnt projector. The projector is trained using metric learning to increase the discrimination of the parameters of the mesh. The values are input to the projector, and the projector outputs a set of values that may better indicate similarity and/or dissimilarity. The processor 20 then uses the set of values in the metric space to search the database, which also includes sets of values in the metric space.

The processor 20 is configured to generating a synthetic topogram. The CT data for the similar patient is deformed to account for differences between the current patient and the patient from the database with similar size and/or shape. The synthetic topogram is generated from this deformed set of CT data. Alternatively, a topogram from the similar patient is generated without deformation of the CT volume.

The processor 20 is configured to configure the CT system 16. Settings from the matched patient of the database are used as settings of the CT system 16 for the current patient. The CT system 16 is configured with an iso-center, scan range, or other setting for the current patient. The settings may be adapted or adjusted to account for differences in the size and/or shape of the current patient with the matched patient. In other embodiments, the processor 20 determines the settings from the synthetic topogram. The CT system 16 is configured using the settings determined from the synthetic topogram. In yet another embodiment, the synthetic topogram is presented to the user. The user then inputs the settings of the CT system 16 based on the presented synthetic or regular topogram from the matched patient.

The memory 22 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 22 is part of the CT system 16, part of a computer associated with the processor 20, part of a database, part of another system, a picture archival memory, or a standalone device.

The memory 22 stores data used by the processor 20. For example, the memory 22 stores the database, including the parameters from the fitting and/or in a metric space. Medical scan data for the database, settings, topograms, fitted meshes, and/or other database information are stored. The memory 22 or a different memory stores the depth data, fitted mesh, extracted parameter values, projected parameter values in metric space, match information, and/or CT scan settings for a current patient. Any data used, input to, output by, or created for the acts discussed herein may be stored in the memory 22 or another memory.

The memory 22 or other memory is alternatively or additionally a computer readable storage medium storing data representing instructions executable by the programmed processor 20 and/or CT system 16 for scan data retrieval and/or scanning a current patient. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 24 is a liquid crystal display (LCD), an organic light emitting diode (OLED), a flat panel display, a solid state display, a cathode ray tube (CRT), a projector, a printer, or other now known or later developed display device for outputting a match, settings, topogram, synthetic topogram, fitted mesh, parameters or other information. The display 24 may be part of a user interface. A value or image based on the fitting, matching, or deformation may be output to the user on the display 24.

The display 24 is configured by a display plane buffer or data provided by the processor 20. The display 24 is configured to indicate the match of the mesh of the current patient with the mesh of a patient from the database. Other matched representations may be indicated, such as values of parameters, metric space values, topograms, synthetic topograms, and/or settings for the CT system 16. The match is indicated by providing information from the match.

The CT system 16 is a CT scanner with an x-ray source and detector connected on a gantry that moves relative to a patient bed. The patient bed includes robotics or motors for moving the patient into or relative to a z axis through the bore and up and down within the bore. The CT system 16 scans the patient over a range along the longitudinal axis of the patient with part of the patient positioned in an iso-center of the bore. The CT system 10 scans the body of the patient based on spatial information corresponding to the matched patient. The spatial settings for the matched patient, from a topogram for the similar patient, and/or from a synthetic topogram are used by the CT system 16 to scan the current patient.

In alternative embodiments, an MR, PET, SPECT, or other medical imaging system is used instead of the CT system 16. The same or different type or modality of medical scanner is used for mesh fitting to the patients of the database and scanning the current patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for scan data retrieval, the method comprising:
    measuring depths relative to a surface of a patient with a depth sensor;
    fitting a first mesh to the depths;
    searching for a second mesh in a database of meshes fit to medical scan data from different patients, the searching based on a similarity of values of parameters of the first mesh and values of parameters of the meshes in the database; and
    configuring a medical scanner to scan the patient, the configuring being based, at least in part, on scan parameters derived from one of the different patients corresponding to the second mesh.

2. The method of claim 1, wherein the measuring the depths comprises measuring with an optical depth camera while the patient is on a bed of the medical scanner.

3. The method of claim 1, wherein the fitting of the first mesh to the depths comprises fitting the first mesh as a parameterized deformable model.

4. The method of claim 1, wherein the fitting of the first mesh to the depths comprises:
    detecting a plurality of landmarks represented in the depths relative to the surface of the patient;
    deforming a template mesh to the plurality of landmarks; and
    fitting the template mesh as deformed to the depths.

5. The method of claim 1, wherein the meshes fit to the medical scan data comprise meshes fit to computed tomography data representing a skin of the different patients.

6. The method of claim 1, wherein the meshes fit to the medical scan data comprise meshes fit with a parameterized deformable model.

7. The method of claim 1, wherein the searching comprises comparing the values of the parameters representing the first mesh with the values of the parameters representing the meshes fit to the medical scan data from the different patients.

8. The method of claim 7, wherein the searching comprises comparing measures of patient shape as the scan parameters.

9. The method of claim 7, wherein the searching comprises comparing principle component analysis coefficients as the scan parameters.

10. The method of claim 7, wherein the comparing the values of the parameters representing the first mesh with the values of the parameters representing the meshes fit to the medical scan from the different patients comprises projecting the values of both the parameters to a metric space and comparing in the metric space.

11. The method of claim 1, wherein the configuring comprises configuring a scan range, an iso center, or a scan range and an iso center for the patient.

12. The method of claim 1, further comprising:
    deforming a volume for the medical scan data of the one of the different patients based on the first mesh; and
    generating a topogram from the deformed volume;
    wherein the configuring comprises configuring based on the topogram.

* * * * *